United States Patent [19]

Rhoades

[11] Patent Number: 5,014,692

[45] Date of Patent: May 14, 1991

[54] SELF-MANIPULATABLE ASSEMBLY FOR MOVING A LEG IN A CAST

[76] Inventor: Janice I. Rhoades, P.O. Box 1069, Estero, Fla. 33928-1069

[21] Appl. No.: 611,455

[22] Filed: Nov. 13, 1990

Related U.S. Application Data

[63] Continuation of Ser. No. 380,461, Jul. 17, 1989, abandoned.

[51] Int. Cl.⁵ .............................................. A61F 5/04
[52] U.S. Cl. ..................................... 128/83; 128/882; 272/71; 272/143; 224/901
[58] Field of Search ................. 128/80 R, 83, 84 R, 128/165, 878, 882; 272/71, 143; 224/901, 913, 917

[56] References Cited

U.S. PATENT DOCUMENTS

| | | | |
|---|---|---|---|
| 4,014,327 | 3/1977 | Spiro | 128/165 |
| 4,337,938 | 7/1982 | Rodriguez | 272/143 |
| 4,470,528 | 9/1984 | Dyess | 224/901 |
| 4,854,313 | 8/1989 | Kloepper | 128/882 |

Primary Examiner—Randall L. Green
Assistant Examiner—Paul Prebilic
Attorney, Agent, or Firm—Merrill N. Johnson

[57] ABSTRACT

A self-manipulatable assembly for moving a person's leg encased from the thigh to the foot in a surgical cast. The assembly includes an elongated first strap made of a non-elastic flexible material extending from the ankle portion to the thigh portion of the cast, a second strap made of flexible hook and loop self-locking material encircling the ankle portion of the cast and securing one end of the first strap, and a third strap made of flexible hook and loop self-locking material encircling the thigh portion of the cast and securing the other end of the first strap. The length of the first strap being greater than the distance between the second and third straps.

4 Claims, 1 Drawing Sheet

SELF-MANIPULATABLE ASSEMBLY FOR MOVING A LEG IN A CAST

This is a continuation of copending application Ser. No. 380,461, filed July 17, 1989, now abandoned.

BACKGROUND AND SUMMARY OF THE INVENTION

My invention relates generally to post-surgical appliances and more particularly to an appliance for safely and easily moving a person's leg encased in a surgical cast.

A person whose leg is encased in a cast following surgery or other medical treatment of the leg is usually unable by him or herself to move the leg from one position to another, especially if the cast extends from the thigh to the foot. Whether the person is lying in bed or sitting in a wheelchair, assistance from a nurse or another person is necessary to move the encased leg from one position to a hopefully more comfortable or convenient position.

So far as I am aware there is no known appliance or assembly available which will permit the person whose leg is encased in a thigh-to-foot surgical cast to move his or her leg from one position to another without outside help.

It is an object of my invention to provide a self-manipulatable appliance or assembly for moving a person's leg encased in a cast.

A further object of my invention is to provide a simple and safe appliance which can easily be attached to a thigh-to-foot cast to enable the person to move his or her leg and cast without outside assistance.

Put most simply, my invention for self movement of a person's leg encased in a cast is an assembly made up of three components. First, a strap of flexible but non-stretchable material such as denim or sailcloth preferably about three inches wide and four feet in length. This first strap should have a closed loop on each end. Next, two identical flexible straps preferably made of or with loop and hook self-locking sections. These two straps may be about an inch wide and about three or more feet in length.

To install the assembly, one of the two straps of self-locking material is fitted through one of the closed loops of the first strap and wrapped around the thigh portion of the leg cast. Then the second strap of self-locking material is fitted through the closed loop in the other end of the first strap and wrapped around the ankle portion of the leg cast.

The length of the first strap between the thigh portion and the ankle portion of the cast is somewhat greater than the distance between the two cast-encircling straps, so that the first strap becomes a "handle" which can be grasped by the person's hand to use the power of his arm to move his leg and cast from one position to another without outside assistance.

DETAILED DESCRIPTION OF THE PREFERRED EMODIMENT

Figure 1:
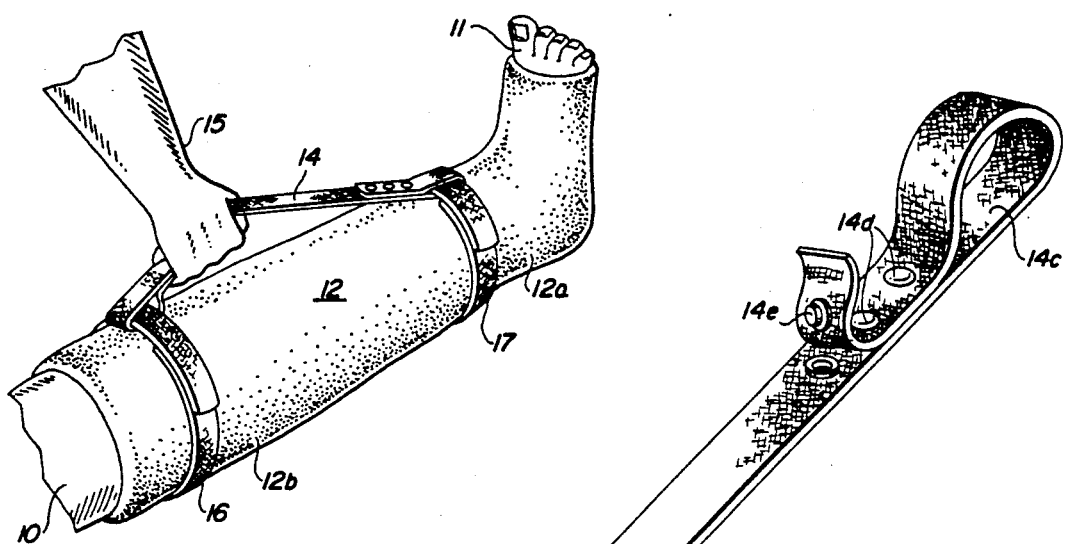
FIG. 1 is a perspective view showing the movement of a preferred embodiment of my self-manipulatable assembly attached to a foot-to-thigh leg cast.

Referring to the appended drawings, FIG. 1 shows a broken away view of a leg 10 and foot 11 encased in a rigid surgical cast 12. Cast 12 is of such weight and so constructed that it is usually impossible for the person whose leg is in the the cast to move the leg without outside assistance.

Figure 3:
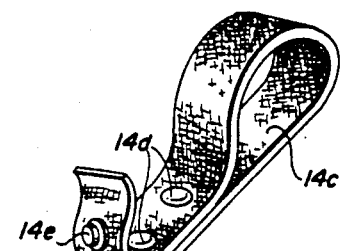
FIG. 3 is a perspective view of the handle of the self-manipulatable assembly shown in FIG. 1.

My invention permits the person to use his arm and shoulder muscles to move the cast-encased leg without outside help. The self-manipulatable assembly includes three cooperating components. First, a preferable adjustable strap or "handle" 14 made of a flexible but non-stretchable material such as woven belting or denim. Handle 14 has a loop 14a on one end closed by stitching 14b as shown in FIG. 3.

Handle 14 also has a closed loop 14c on its other end and the length of the handle is adjustable by a series of cooperating snaps 14d and receptacles 14e. Alternatively, handle 14 can be made adjustable by replacing snaps 14d and receptacles 14e with VELCRO® hook and loop self-locking sections on handle 14.

Figure 2:
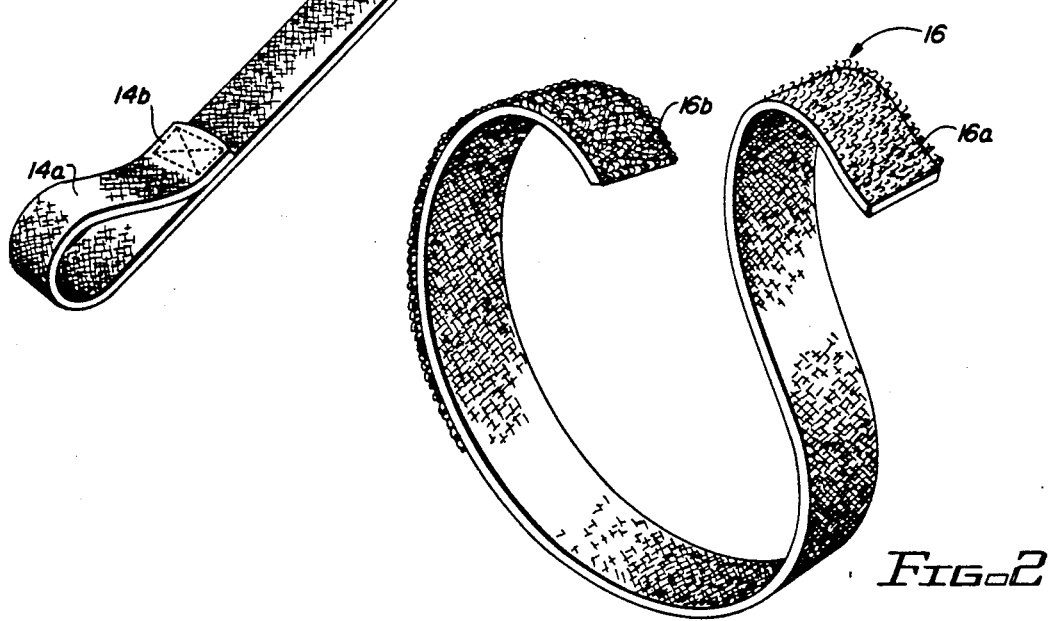
FIG. 2 is a perspective view of one of the straps shown in FIG. 1 used to attach the handle onto the leg cast.

In addition to handle 14, my self-manipulatable assembly includes two similar straps 16 and 17 as shown in FIG. 2. Straps 16 and 17 are preferably made of a flexible but non-stretchable material such as denim about one inch wide and three or more feet in length.

When wrapped around the thigh portion 12b and ankle portion 12a respectively of leg cast 12, straps 16 and 17 are locked into position by VELCRO® hook and loop sections 16a and 16b as best shown in FIG. 2.

My assembly is installed as shown in FIG. 1 by first fitting strap 16 through look 14a of the handle and then wrapping strap 16 around thigh portion 12b of the leg cast. Then loop 14c is closed by adjusting the length of handle 14 to somewhat greater than the distance between the thigh and ankle portions of cast 12. Strap 17 is then fitted through closed loop 14c and wrapped around the ankle portion 12a of the cast.

Now the person whose leg is encased in cast 12 can grasp handle 14 with his or her hand 15 as shown in FIG. 1 and using the muscles of his or her arm and shoulder to move the leg and cast from one position to another without outside assistance.

While I have shown and described a preferred enbodiment of my self-manipulatable assembly, such description is not intended to limit the scope of my invention whose scope is limited only by the appended claims.

I claim:

1. A self-manipulatable assembly for moving a person's leg encased in a cast extending from the person's thigh to his foot comprising an elongated first strap made entirely of flexible but nonstretchable fabric material extending from the ankle portion to the thigh portion of the cast, said first strap forming at each of its ends a closed loop, a second strap made entirely of flexible fabric material encircling the ankle portion of the cast and said strap itself passing through the closed loop on one end of the elongated first strap, a third strap made entirely of flexible fabric material encircling the thigh portion of the cast and said strap itself passing through the closed loop on the opposite end of the elongated first strap, the length of the elongated first strap between the second and third straps being somewhat longer than the distance between the second and third straps.

2. A self-manipulatable assembly as set forth in claim 1 in which the second and third straps include two mating sections made of flexible hook and loop self-locking material.

3. A self-manipulatable assembly as set forth in claim 1 in which one of the closed loops is adjustable so that the length of the first strap between the two closed loops can be varied.

4. A self-manipulatable assembly for moving a person's leg encased in a cast extending from the person's thigh to his foot comprising an elongated first strap made entirely of flexible but nonstretchable fabric material extending from the ankle portion to the thigh portion of the cast, said first strap forming at each of its ends a closed loop, a second strap made entirely of flexible fabric material and at least in part of flexible hook and loop self-locking material encircling the ankle portion of the cast and said strap itself passing through the closed loop on one end of the elongated first strap, a third strap made entirely of flexible fabric material and at least in part of flexible hook and loop self-locking material encircling the thigh portion of the cast and said strap itself passing through the closed loop on the opposite end of the elongated first strap, the length of the elongated first strap between the second and third straps being somewhat longer than the distance between the second and third straps.

* * * * *